(12) United States Patent
Shiraki et al.

(10) Patent No.: US 6,222,085 B1
(45) Date of Patent: Apr. 24, 2001

(54) CATALYST FOR DEHYDROGENATION OF ALKYLAROMATIC HYDROCARBON, PROCESS FOR PRODUCING THE CATALYST, AND PROCESS FOR PRODUCING VINYLAROMATIC HYDROCARBON BY USING THE CATALYST

(75) Inventors: Yasushi Shiraki; Kichinari Kawamura; Fumitaka Honjo, all of Tokuyama (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/381,644

(22) PCT Filed: Mar. 23, 1998

(86) PCT No.: PCT/JP98/01235

§ 371 Date: Nov. 4, 1999

§ 102(e) Date: Nov. 4, 1999

(87) PCT Pub. No.: WO98/43734

PCT Pub. Date: Oct. 8, 1998

(30) Foreign Application Priority Data

Mar. 31, 1997 (JP) ........................................... 9-79734

(51) Int. Cl.⁷ ............................. C07C 2/64; B01J 23/745; B01J 23/04
(52) U.S. Cl. ........................ 585/444; 585/445; 502/338; 502/344; 502/330
(58) Field of Search .................................... 585/444, 445; 502/338, 344, 330

(56) References Cited

U.S. PATENT DOCUMENTS 5,824,831 * 10/1998 Shiraki et al. ........................ 585/444

FOREIGN PATENT DOCUMENTS

0086100 * 7/1995 (EP) .
07178340A * 7/1995 (JP) .

* cited by examiner

Primary Examiner—Walter D. Griffin
Assistant Examiner—Thuvan D. Dang
(74) Attorney, Agent, or Firm—Oblon, Spivak, McClelland, Maier & Neustadt, P.C.

(57) ABSTRACT

A solid catalyst containing a potassium component and an iron oxide component, which is such that the ratio of the pore volume of pores therein having a diameter of from 20 to 100 nm to that of pores therein having a diameter of up to 100 nm falls between 0.7/1 and 0.9/1 and which is stable to oxygen-containing vapor, is favorably used as a dehydrogenation catalyst in producing vinyl-aromatic hydrocarbons from alkyl-aromatic hydrocarbons. The catalyst has high initial activity and good initial selectivity and its life is long. In addition, it is easy to handle. The catalyst may be produced by reducing a potassium component-containing iron oxide composition with hydrogen at a temperature falling between 350 and 600° C., and then oxidizing it with an oxygen molecules-containing vapor at a temperature falling between 250 and 500° C.

6 Claims, No Drawings

CATALYST FOR DEHYDROGENATION OF ALKYLAROMATIC HYDROCARBON, PROCESS FOR PRODUCING THE CATALYST, AND PROCESS FOR PRODUCING VINYLAROMATIC HYDROCARBON BY USING THE CATALYST

BACKGROUND OF THE INVENTION

1. Field of the Invention

The present invention relates to a catalyst for dehydrogenation of alkyl-aromatic hydrocarbons, to a method for producing it, and to a method of using it for producing vinyl-aromatic hydrocarbons.

2. Description of the Related Art

Heretofore, vinyl-aromatic hydrocarbons such as styrene have been produced through dehydrogenation of alkyl-aromatic hydrocarbons in the presence of a catalyst, for which generally used is an iron oxide-type catalyst as the catalyst (catalyst for dehydrogenation).

Up to now, various attempts have been made for improving the capabilities of the catalyst for dehydrogenation, for example, by adding thereto various catalyst components thereby to enhance the dehydrogenation activity of the catalyst and to prolong the life thereof. In addition, known are methods of pre-treating the catalyst for improving its capabilities.

Regarding these, we, the present applicant have disclosed a catalyst for dehydrogenation in Japanese Patent Laid-Open No. 178340/1995, which is produced by reducing an iron oxide-type catalyst that comprises iron oxide and potassium oxide added thereto, with hydrogen at a temperature falling between 350 and 600° C.

The catalyst is favorable to production of vinyl-aromatic hydrocarbons, as its initial activity is high and its life is long. However, it has become known that the catalyst generates heat when exposed to air and therefore must be carefully handled so as to evade its exposure to air when filled into reactors.

The present invention is to solve the problems in the related art as above, and its object is to provide a catalyst for dehydrogenation of alkyl-aromatic hydrocarbons, which has high activity and good selectivity for the intended dehydrogenation and has a long life and which can be handled with no difficulty, and also to provide a method for producing it.

Another object of the invention is to provide a method of using the catalyst for producing vinyl-aromatic compounds, in which the catalyst exhibits high activity and good selectivity while maintaining its capabilities for a long period of time and can be handled with no difficulty.

SUMMARY OF THE INVENTION

We, the present inventors have assiduously studied so as to solve the problems in the related art as above. As a result, we have found that a catalyst to be prepared by reducing a potassium component-containing iron oxide composition with hydrogen at a relatively low temperature followed by oxidizing it with a vapor that contains oxygen molecules has extremely good capabilities for dehydrogenation of alkyl-aromatic hydrocarbons, that the life of the catalyst is extremely long, and that the catalyst is stable in oxygen-containing vapors such as air. On the basis of these findings, we have completed the present invention.

Specifically, the gist of the invention is summarized as follows:

(1) A catalyst for dehydrogenation of alkyl-aromatic hydrocarbons, which is a solid catalyst containing a potassium component and an iron oxide component and which is characterized in that the ratio of the pore volume of pores therein having a diameter of from 20 to 100 nm to that of pores therein having a diameter of up to 100 nm falls between 0.7/1 and 0.9/1 and that the catalyst is stable to oxygen.

(2) A method for producing a catalyst for dehydrogenation of alkyl-aromatic hydrocarbons, which comprises reducing a potassium component-containing iron oxide composition with hydrogen at a temperature falling between 350 and 600° C., followed by oxidizing it with a vapor that contains oxygen molecules at a temperature falling between 250 and 500° C.

(3) The method for producing a catalyst for dehydrogenation of alkyl-aromatic hydrocarbons as in above (2), wherein the oxygen molecules-containing vapor is air.

(4) A method for producing vinyl-aromatic hydrocarbons by dehydrogenating alkyl-aromatic hydrocarbons in the presence of a catalyst, in which is used the catalyst of above (1), or the catalyst as produced according to the method of above (2) or (3).

DETAILED DESCRIPTION OF THE INVENTION

The invention is described in detail hereinunder.

First described is the iron oxide composition which is the starting material in the method of producing the catalyst of the invention.

The iron oxide composition indispensably contains a potassium component, and generally has the capabilities for catalyzing dehydrogenation of alkyl-aromatic hydrocarbons. For producing it, for example, employable is a method of mixing iron oxide ($Fe_2O_3$) and a potassium compound, followed by drying and baking the resulting mixture.

As iron oxide to be used herein, preferred is $\alpha$-$Fe_2O_3$; and as the potassium component, preferred are potassium carbonate and potassium oxide.

The iron oxide content of the iron oxide composition preferably falls between 40 and 95% by weight, and it is desirable that the composition contains from 5 to 30% by weight of a potassium component such as potassium oxide. The composition may contain potassium ferrite. Potassium ferrite is $K_2Fe_2O_4$ (or $KFeO_2$). The presence of potassium ferrite in the composition could be confirmed through X-ray diffractometry.

The iron oxide composition may further contain any other component of, for example, minor alkaline earth metal compounds such as calcium oxide (generally, in an amount of smaller than 3% by weight) and chromium oxide (generally, in an amount of smaller than 4% by weight), and also magnesium oxide in an amount of not larger than about 10% by weight, cerium oxide in an amount of not larger than about 6% by weight, and molybdenum oxide in an amount of not larger than about 3% by weight. Apart from those, it may also contain rare earth metal compounds such as lanthanum oxide.

For producing the catalyst of the invention, the iron oxide composition is reduced and then oxidized. The treatment for the catalyst production is effected in a vapor phase. Prior to the treatment, therefore, it is convenient to previously shape the iron oxide composition in accordance with the shape of the intended catalyst. The catalyst may have any desired shape. In general, it is columnar, having a diameter of from 2 mm to 4 mm or so and a length of from 3 to 10 mm or so.

Next described is the reduction with hydrogen of the iron oxide composition. The iron oxide composition may be reduced with hydrogen at a temperature falling between 350 and 600° C., but preferably between 400 and 500° C. If the temperature for the reduction is lower than 350° C., the reduction rate will be greatly lowered and the intended degree of reduction could not be obtained. Even if the iron oxide composition having been reduced to such a low degree of reduction is thereafter oxidized in a suitable manner, the resulting catalyst will be readily deactivated and could not have a long life. On the other hand, if the temperature for the reduction is higher than 600° C., the activity of the resulting catalyst will be low even if the reduced composition is thereafter oxidized in a suitable manner. The time for the reduction depends on the temperature for it, but is generally not shorter than 1 hour, preferably from 5 to 30 hours. When the temperature for the reduction is low, it is recommended to increase the hydrogen flow rate or to prolong the time for the reduction.

Hydrogen to be used for the reduction may contain any other vapor inert to dehydrogenation, such as nitrogen or methane. It may also contain steam, for which the molar ratio of hydrogen to water ($H_2/H_2O$) is preferably not lower than 0.05, more preferably not lower than 0.5.

The hydrogen flow rate is preferably not lower than 5 $hr^{-1}$, more preferably between 20 and 300 $h^{-1}$, in terms of the gaseous hourly space velocity (GHSV) of pure hydrogen. The pressure for the reduction is not specifically defined. If desired, the reduction may be effected under elevated pressure or reduced pressure.

Preferably, the reduced composition is such that the ratio of the pore volume of pores therein having a diameter of from 20 to 100 nm to that of pores therein having a diameter of up to 100 nm falls between 0.7/1 and 0.9/1, or that is, the ratio of (pore volume of pores therein having a diameter of from 20 to 100 nm)/(pore volume of pores therein having a diameter of up to 100 nm)=0.7/1 to 0.9/1. Further in other words, the proportion of the pore volume of pores in the reduced composition having a diameter of from 20 to 100 nm to that of pores therein having a diameter of up to 100 nm is from 70 to 90%.

Also preferably, the reduced composition has a specific surface area of from 1.0 to 2.5 $m^2/g$, more preferably from 1.5 to 2.0 $m^2/g$. The specific surface area and the pore volume as referred to herein may be determined through isovolumetric vapor adsorption.

Next described is the oxidation that follows the previous reduction. In the method of producing the catalyst of the invention, the catalyst produced is stabilized to oxygen through the oxidation, while maintaining its original capabilities for catalyzation.

The temperature for the oxidation may fall between 250 and 500° C., but preferably between 300 and 450° C., more preferably between 350 and 400° C. If the temperature for the oxidation is lower than 250° C., the stability to oxygen of the catalyst produced will be poor and the catalyst will be readily deactivated and could not have a long life. On the other hand, if the temperature for the oxidation is higher than 500° C., the activity of the catalyst produced will be low and the catalyst will be readily deactivated. The time for the oxidation depends on the temperature for it, but is generally not shorter than 1 hour, preferably from 3 to 30 hours. When the temperature for the oxidation is low, it is recommended to increase the flow rate of the oxygen molecules-containing vapor to be applied to the reduced composition, or to prolong the time for the oxidation. However, if the temperature for the oxidation is lower than 250° C., the effect of the invention could not be attained even though the time for the oxidation is prolonged. If the time for the oxidation is shorter than 1 hour, the catalyst produced could not be well stabilized to oxygen. On the other hand, even if the oxidation is effected for a longer period of time over 30 hours, no further improvement in the catalyst activity and in the catalyst life could be expected.

The vapor for the oxidation must contain oxygen molecules. Even though containing oxygen, a vapor not containing molecular oxygen such as steam is useless in the invention, since the reduced composition as oxidized with the vapor of that type could not turn into a catalyst having a long life. Preferably, the oxygen content of the vapor for the oxidation falls between 1 and 50% by volume, more preferably between 2 and 22% by volume. If it is smaller than 1% by volume, the temperature for the oxidation must be high and the time for it must be long. On the other hand, the vapor having an oxygen content of larger than 50% by volume will be unfavorable as it is not safe and is difficult to handle.

The vapor for the oxidation may contain any inert gas such as nitrogen, helium and argon. Air is preferred as the vapor, since it is easily available, safe and inexpensive.

The flow rate of the oxygen molecules-containing vapor for the oxidation is preferably not lower than 50 $hr^{-1}$, more preferably between 200 and 800 $h^{-1}$, in terms of the gaseous hourly space velocity (GHSV) of air. However, if the oxidation vapor flow rate is as above in the initial stage of oxidation, the reaction system will generate heat to have a temperature of higher than 500° C. Therefore, in the initial stage of oxidation, GHSV of the oxidation vapor must be so controlled that the reaction system is not heated above 500° C. The pressure for the oxidation is not specifically defined. If desired, the oxidation may be effected under elevated pressure or reduced pressure.

Preferably, the catalyst thus obtained after the oxidation is such that the ratio of the pore volume of pores therein having a diameter of from 20 to 100 nm to that of pores therein having a diameter of 0 to 100 nm falls between 0.7/1 and 0.9/1, or that is, the ratio of (pore volume of pores therein having a diameter of from 20 to 100 nm)/(pore volume of pores therein having a diameter of up to 100 nm)=0.7/1 to 0.9/1. Further in other words, the proportion of the pore volume of pores in the catalyst having a diameter of from 20 to 100 nm to that of pores therein having a diameter of up to 100 nm is from 70 to 90%.

Also preferably, the catalyst has a specific surface area of from 1.0 to 2.5 $m^2/g$, more preferably from 1.5 to 2.0 $m^2/g$. The specific surface area and the pore volume may be determined in the same manner as above.

As in the above, it is desirable that the specific surface area of the catalyst falls between 1.0 and 2.5 $m^2/g$ and that the pore distribution in the catalyst is so controlled that the number of micro-pores therein is small while the number of macro-pores therein is large.

The catalyst for dehydrogenation of alkyl-aromatic hydrocarbons of the invention is a solid catalyst that contains a potassium component and an iron oxide component. In the catalyst, the ratio of the pore volume of pores having a diameter of from 20 to 100 nm to that of pores having a diameter of 0 to 100 nm falls between 0.7/1 and 0.9/1. The catalyst is stable to oxygen.

In the catalyst, the potassium component is not specifically defined and may be any of potassium oxide or potassium carbonate, or may also be potassium ferrite. The iron oxide component generally comprises iron oxide ($Fe_2O_3$), and this is the essential component of the catalyst. Regarding their proportions in the catalyst, it is desirable that the iron oxide component is in an amount of from 40 to 95% by weight and the potassium component is in an amount of from 5 to 30% by weight. If the amount of the potassium component in the catalyst is smaller than 5% by weight, the activity and also the selectivity of the catalyst will be poor; but if larger than 30% by weight, the activity of the catalyst, especially that in the initial stage of dehydrogenation with it will be low.

The catalyst of the invention may further contain any other component of, for example, minor alkaline earth metal compounds such as calcium oxide (generally, in an amount of smaller than 3% by weight) and chromium oxide (generally, in an amount of smaller than 4% by weight), and also magnesium oxide in an amount of not larger than about 10% by weight, cerium oxide in an amount of not larger than about 6% by weight, and molybdenum oxide in an amount of not larger than about 3% by weight. Apart from those, it may also contain rare earth metal compounds such as lanthanum oxide.

The specific surface area and the pore volume of the catalyst may be determined in the same manner as above. As so defined hereinabove, the pore volume ratio of the pores existing in the catalyst must fall between 0.7 and 0.9. If the ratio is smaller than 0.7, the catalyst will be readily deactivated; but if larger than 0.9, the activity of the catalyst will be unfavorably low. Preferably, the specific surface area of the catalyst falls between 1.0 and 2.5 $m^2/g$, more preferably between 1.5 and 2.0 $m^2/g$. If its specific surface area oversteps the range of from 1.0 to 2.5 $m^2/g$, the activity of the catalyst will be low.

The catalyst of the invention is stable to oxygen, and this means that the catalyst generates little heat when exposed to air. Concretely, the stability to oxygen of the catalyst may be demonstrated as follows: A thermocouple is fixed to the bottom of an evaporating dish having a diameter of 6 cm, the dish with the thermocouple thus fixed thereto is kept in air at room temperature, and 5 g of a sample of the catalyst is put in the dish and left as it is for 10 minutes. Then, the temperature of the sample in the dish is measured. In that condition, when the temperature increase after 10 minutes is not larger than 5° C. or so, the stability to oxygen of the catalyst is good.

The catalyst of the invention may be produced, for example, according to the production method mentioned hereinabove.

In the method for producing vinyl-aromatic hydrocarbons of the invention, the catalyst for dehydrogenation of the invention mentioned above, or the catalyst for dehydrogenation as produced according to the method of the invention also mentioned above is used for dehydrogenating alkyl-aromatic hydrocarbons to give vinyl-aromatic hydrocarbons.

As the starting alkyl-aromatic hydrocarbons, used are aromatic hydrocarbons having 1 or 2 alkyl groups capable of forming vinyl groups through dehydrogenation. Concretely, they include ethylbenzene, diethylbenzene, ethyltoluene, and ethylnaphthalene. In those, the benzene ring may have any other substituents not participating in dehydrogenation, for example, an alkyl group such as a methyl group, and a halogen atom such as a chlorine atom.

Regarding the condition for the dehydrogenation, the temperature generally falls between 550 and 650° C., but preferably between 580 and 640° C. The pressure generally falls between 200 and 600 Torr, but preferably between 300 and 500 Torr. The dehydrogenation requires steam, and the ratio of steam to the starting alkyl-aromatic hydrocarbon to be dehydrogenated (steam/alkyl-aromatic hydrocarbon, by weight) generally falls between 1.0 and 3.0, but preferably between 1.2 and 2.0. The liquid hourly space velocity (LHSV) of the alkyl-aromatic hydrocarbon generally falls between 0.2 and 20 $hr^{-1}$, but preferably between 0.3 and 1.0 $hr^{-1}$.

As in the above, vinyl-aromatic hydrocarbons are produced from alkyl-aromatic hydrocarbons, for example, styrene is produced from ethylbenzene.

The invention is described in more detail with reference to the following Examples, which, however, are not intended to restrict the scope of the invention.

In the following Examples and Comparative Examples, used was the following iron oxide composition as the starting material. Also in those, the following reaction tube was used in preparing catalyst samples and in producing styrene.

First prepared was an iron oxide composition from iron oxide ($\alpha$-$Fe_2O_3$) and potassium carbonate ($K_2CO_3$). Precisely, 450 g of iron oxide and 50 g of potassium carbonate (ratio by weight of the two=9/1) were put into an agate mortar, well mixed therein, and then well kneaded with water added thereto, and the resulting paste was introduced into a vertical extruder having a die size (diameter) of 3 mm and extruded out therethrough. The resulting molding was dried in air at a temperature falling between 120 and 200° C. for 20 hours, and then baked in an air atmosphere in a muffle furnace, at 800° C. for 4 hours to obtain an iron oxide composition.

As the reactor tube, a one inch tube (inner diameter: 21.4 mm) having a length of 60 cm was used. 100 cc (132 g) of the iron oxide composition prepared previously was filled into the tube. The reactor tube was filled with ⅛ inches alumina balls in the upper layer site of the catalyst bed, and the bottom of the catalyst bed was fixed to a perforated plate. The inner temperature of the reactor tube was controlled by an electric furnace disposed around the outer surface of the reactor tube. The electric furnace had three heating zones separated from each other. A thermocouple protected with a protector tube having an outer diameter of 6 mm was inserted into the reactor tube, with which the temperature in the top, the middle area and the bottom of the catalyst bed was monitored. The temperature in the top and the bottom of the catalyst bed was so controlled that it could be as similar as possible to the reaction temperature in the reactor tube, by controlling each heating zone of the electric furnace. In the reactor tube, the reaction was effected in a down-flow system.

EXAMPLE 1

(1) Preparation of catalyst:

100 cc (132 g) of the iron oxide composition prepared previously was filled into the reactor tube as above, which was then degassed to have a reduced pressure of 460 Torr. Then, nitrogen gas was introduced into the reactor tube at a flow rate of 3 liters/hr. The reactor tube was heated at a heating rate of 100° C./hr, and when it was heated up to 500° C., nitrogen gas being introduced thereinto was switched to hydrogen gas. Hydrogen gas was thus introduced into the reactor tube at a flow rate of 3 liters/hr (GHSV=30 $hr^{-1}$), with which the iron oxide composition in the reactor tube was reduced at 500° C. for 24 hours.

After the composition was thus reduced with hydrogen, the temperature in the reactor tube was lowered to 400° C., and hydrogen gas being introduced into the reactor tube was again switched to nitrogen gas. Then, nitrogen gas introduction was effected for 3 hours, and the reactor tube was thus purged with nitrogen. Next, the flowing gas in the reactor tube was switched to air. Air was introduced into the reactor tube at a flow rate of 3 liters/hr (GHSV=30 hr$^{-1}$) for 2 hours, with which the composition was pre-oxidized. Then, air was further introduced thereinto at a flow rate of 12 liters/hr (GHSV=120 hr$^{-1}$), with which the composition was oxidized for 10 hours. Through the treatment, the composition turned into a catalyst of the invention.

The catalyst thus prepared herein was measured through isovolumetric vapor adsorption, for which was used a measuring device of Belsorp 36 (from Nippon Bell). As a result, the catalyst was found to have a specific surface area of 1.5 m$^2$/g, and a pore volume ratio of pores having a size of from 20 to 100 nm of 0.86. The pore volume ratio of 0.86 means that the ratio of the pore volume of pores in the catalyst having a diameter of from 20 to 100 nm is 86% of the pore volume of pores therein having a diameter of up to 100 nm. 5 g of the catalyst was taken out in air, and kept in an evaporating dish having a diameter of 6 cm, to which was fixed a thermocouple at its bottom, for 10 minutes. In that condition, the catalyst having been kept in the dish did not generate heat.

(2) Production of styrene:

After the catalyst was produced, air introduction into the reactor tube was stopped. Then, steam was introduced thereinto at a flow rate of 150 g/hr, with heating the reactor tube at a heating rate of 100° C./hr. When this was heated up to 550° C., ethylbenzene was introduced thereinto at a flow rate of 100 g/hr. The ratio of steam/ethylbenzene (by weight) was 1.5, and the liquid hourly space velocity (LHSV) of ethylbenzene was 1.0 hr$^{-1}$.

Next, the reactor tube was further heated at a heating rate of 100° C./hr up to 620° C., and kept at the elevated temperature of 620° C. for 3 months (for which dehydrogenation of ethylbenzene was continued). The initial activity of the catalyst, the initial selectivity thereof, and the deactivation rate thereof were determined. The initial activity of the catalyst was indicated by the styrene (SM) concentration (% by weight) in the reaction liquid, and the initial selectivity thereof was indicated by the ratio of the concentration of styrene formed (SM) to the concentration of ethylbenzene converted (ΔEB), SM/ΔEB, in terms of % by weight. The deactivation rate of the catalyst was indicated by the reduction in the styrene concentration in the reaction liquid in one day (ΔSM) (wt. %/day). The styrene concentration (SM) and the concentration of ethylbenzene converted (ΔB) were obtained by analyzing the reaction liquid through gas chromatography. The data obtained are shown in Table 1 below.

EXAMPLE 2

A catalyst was produced in the same manner as in Example 1(1). In this, however, the iron oxide composition was reduced with hydrogen in the same manner as in Example 1(1), and thereafter a mixed gas of air and nitrogen (air/nitrogen=20/80, by volume), but not air only, was applied to the reduced composition for oxidizing it.

The catalyst obtained herein had a specific surface area of 1.7 m$^2$/g, and a pore volume ratio of pores having a size of from 20 to 100 nm of 0.87. The pore volume ratio of 0.87 means that the ratio of the pore volume of pores in the catalyst having a diameter of from 20 to 100 nm is 87% of the pore volume of pores therein having a diameter of up to 100 nm. The catalyst was tested for heat generation, if any, in air, in the same manner as in Example 1(1), but it did not generate heat.

Next, the catalyst was used in producing styrene, also in the same manner as in Example 1, and its initial activity, initial selectivity and deactivation rate were determined. The data are in Table 1.

EXAMPLE 3

A catalyst was produced in the same manner as in Example 1(1). In this, however, the iron oxide composition was reduced with hydrogen in the same manner as in Example 1(1), and thereafter this was oxidized with the inner temperature of the reactor tube being kept at 350° C.

The catalyst obtained herein had a specific surface area of 1.6 m$^2$/g, and a pore volume ratio of pores having a size of from 20 to 100 nm of 0.87. The pore volume ratio of 0.87 means that the ratio of the pore volume of pores in the catalyst having a diameter of from 20 to 100 nm is 87% of the pore volume of pores therein having a diameter of up to 100 nm. The catalyst was tested for heat generation, if any, in air, in the same manner as in Example 1(1), but it did not generate heat.

Next, the catalyst was used in producing styrene, also in the same manner as in Example 1, and its initial activity, initial selectivity and deactivation rate were determined. The data are in Table 1.

Comparative Example 1

A catalyst was produced in the same manner as in Example 1(1). In this, however, the iron oxide composition was reduced with hydrogen in the same manner as in Example 1(1), and thereafter this was oxidized with the inner temperature of the reactor tube being kept at 600° C.

The catalyst obtained herein had a specific surface area of 0.8 m$^2$/g, and a pore volume ratio of pores having a size of from 20 to 100 nm of 0.92. The pore volume ratio of 0.92 means that the ratio of the pore volume of pores in the catalyst having a diameter of from 20 to 100 nm is 92% of the pore volume of pores therein having a diameter of up to 100 nm. The catalyst was tested for heat generation, if any, in air, in the same manner as in Example 1(1), but it did not generate heat.

Next, the catalyst was used in producing styrene, also in the same manner as in Example 1, and its initial activity, initial selectivity and deactivation rate were determined. The data are in Table 1.

Comparative Example 2

A catalyst was produced in the same manner as in Example 1(1). In this, however, the iron oxide composition was reduced with hydrogen in the same manner as in Example 1(1), and thereafter this was oxidized with the inner temperature of the reactor tube being kept at 150° C.

The catalyst obtained herein had a specific surface area of 3.5 m$^2$/g, and a pore volume ratio of pores having a size of from 20 to 100 nm of 0.68. The pore volume ratio of 0.68 means that the ratio of the pore volume of pores in the catalyst having a diameter of from 20 to 100 nm is 68% of the pore volume of pores therein having a diameter of up to 100 nm. The catalyst was tested for heat generation, if any, in air, in the same manner as in Example 1(1), but it did not generate heat.

Next, the catalyst was used in producing styrene, also in the same manner as in Example 1, and its initial activity, initial selectivity and deactivation rate were determined. The data are in Table 1.

Comparative Example 3

A catalyst was produced in the same manner as in Example 1(1). In this, however, the iron oxide composition was reduced with hydrogen in the same manner as in Example 1(1), and thereafter steam, but not air, was applied to the reduced composition for oxidizing it.

The catalyst obtained herein had a specific surface area of 4.0 m$^2$/g, and a pore volume ratio of pores having a size of from 20 to 100 nm of 0.65. The pore volume ratio of 0.65 means that the ratio of the pore volume of pores in the catalyst having a diameter of from 20 to 100 nm is 65% of the pore volume of pores therein having a diameter of up to 100 nm. The catalyst was tested for heat generation, if any, in air, in the same manner as in Example 1(1), but it did not generate heat.

Next, the catalyst was used in producing styrene, also in the same manner as in Example 1, and its initial activity, initial selectivity and deactivation rate were determined. The data are in Table 1.

Comparative Example 4

Styrene was produced in the same manner as in Example 1. In this, however, the iron oxide composition that had been used as the starting material in the Examples and the Comparative Examples mentioned above was used as the catalyst. The initial activity, the initial selectivity and the deactivation rate of the catalyst used herein were determined. The data are in Table 1.

The iron oxide composition used herein as the catalyst had a specific surface area of 2.5 m$^2$/g, and a pore volume ratio of pores having a size of from 20 to 100 nm of 0.69. The pore volume ratio of 0.69 means that the ratio of the pore volume of pores in the catalyst having a diameter of from 20 to 100 nm is 69% of the pore volume of pores therein having a diameter of up to 100 nm. This was tested for heat generation, if any, in air, in the same manner as in Example 1(1), but did not generate heat.

Comparative Example 5

The iron oxide composition was reduced with hydrogen in the same manner as in Example 1. Without being oxidized, this was used in producing styrene.

The catalyst obtained herein had a specific surface area of 1.6 m$^2$/g, and a pore volume ratio of pores having a size of from 20 to 100 nm of 0.86. The pore volume ratio of 0.86 means that the ratio of the pore volume of pores in the catalyst having a diameter of from 20 to 100 nm is 86% of the pore volume of pores therein having a diameter of up to 100 nm. The catalyst was tested for heat generation, if any, in air, in the same manner as in Example 1(1). In this test, the temperature indicated by the thermocouple varied from 20° C. to 80° C. This means that the catalyst tested generated much heat.

Next, the catalyst was used in producing styrene, also in the same manner as in Example 1, and its initial activity, initial selectivity and deactivation rate were determined. The data are in Table 1.

TABLE 1

| | Condition for Oxidation | | | Properties of Catalyst | | | |
|---|---|---|---|---|---|---|---|
| | Oxidizing Agent | Temperature (° C.) | Time (hr) | Initial Activity (wt. %) | Initial Selectivity (wt. %) | Deactivation Rate (%/day) | Heat Generation in Exposure to Air |
| Example 1 | air | 400 | 10 | 71.1 | 96.1 | −0.034 | no |
| Example 2 | air/nitrogen | 400 | 10 | 71.2 | 95.9 | −0.032 | no |
| Example 3 | air | 350 | 24 | 71.0 | 96.0 | −0.033 | no |
| Comparative Example 1 | air | 600 | 10 | 67.9 | 96.0 | −0.051 | no |
| Comparative Example 2 | air | 150 | 24 | 70.3 | 95.8 | −0.063 | no |
| Comparative Example 3 | steam | 400 | 10 | 69.8 | 95.3 | −0.068 | no |
| Comparative Example 4 | — | — | — | 69.6 | 95.4 | −0.083 | no |
| Comparative Example 5 | — | — | — | 71.2 | 96.1 | −0.033 | yes |

From Table 1, the following were confirmed:
(i) The catalysts as produced from an iron oxide composition through reduction with hydrogen followed by oxidation at 400° C. (Examples 1 and 2) or at 350° C. (Example 3) are much better than the catalyst of the iron oxide composition itself not subjected to reduction and oxidation (Comparative Example 4) in that the initial activity of the former is higher in some degree, the deactivation rate of the former is much smaller, or that is the deactivation rate of the former is from ⅓ to ½ of that of the latter, and the selectivity of the former is higher.
(ii) When an iron oxide composition is reduced with hydrogen and then oxidized at a high temperature (600° C.), as in Comparative Example 1, the resulting catalyst is not good since its deactivation rate is high and its initial activity is low.
(iii) When an iron oxide composition is reduced with hydrogen and then oxidized at a low temperature (150° C.), as in Comparative Example 2, a good catalyst could not be obtained even though the time for oxidation is 24 hours. The deactivation rate of the catalyst obtained is large.

(iv) When steam is used as the oxidizing agent, a good catalyst could not be obtained. The initial activity of the catalyst obtained is lowered in some degree, and the deactivation rate thereof is large (Comparative Example 3).

(v) The catalysts of such that the ratio of the pore volume of pores therein having a diameter of from 20 to 100 nm to that of pores therein having a diameter of 0 to 100 nm falls between 0.7/1 and 0.9/1 (Examples 1 to 3, Comparative Example 5) have high initial activity and good initial selectivity, and their deactivation rate is small. However, the catalyst obtained in Comparative Example 5 generates much heat when exposed to air, and must be handled with care.

(vi) The catalysts having a specific surface area of from 1.0 to 2.0 $m^2/g$ (Examples 1 to 3, Comparative Example 5) have high initial activity and good initial selectivity, and their deactivation rate is small. However, the catalyst obtained in Comparative Example 5 generates much heat when exposed to air, and must be handled with care.

As demonstrated hereinabove, the catalyst of the invention and also the catalyst as produced according to the production method of the invention have increased initial activity and increased initial selectivity and their life is much prolonged, as compared with any other catalysts overstepping the scope of the invention. In addition, the stability to oxygen of the catalysts falling within the scope of the invention is much increased. Therefore, the catalyst of the invention and also the catalyst as produced according to the production method of the invention are extremely favorable to dehydrogenation of alkyl-aromatic hydrocarbons.

In the method of producing vinyl-aromatic hydrocarbons of the invention, the catalyst falling within the scope of the invention is used for dehydrogenating alkyl-aromatic hydrocarbons. Therefore, according to the method, vinyl-aromatic hydrocarbons are efficiently produced for a long period of time. In addition, the catalyst to be used in the method is highly stable to oxygen, and is easy to handle.

While the invention has been described in detail and with reference to specific embodiments thereof, it will be apparent to one skilled in the art that various changes and modifications can be made therein without departing from the spirit and scope thereof.

What is claimed is:

1. In a catalyst for dehydrogenation of alkali-aromatic hydrocarbons comprising a solid catalyst containing a potassium component and an iron oxide component and which is characterized in that the ratio of the pore volume of pores therein having a diameter of from 20 to 100 nm to that of pores therein having a diameter of from 0 to 100 nm falls between 0.7/1 and 0.9/1, the improvement wherein said catalyst has been pretreated by reducing a potassium component-containing iron oxide composition with hydrogen at a temperature of 350 and 600° C., followed by oxidizing it with oxygen containing vapor at a temperature of 250 and 500° C., the catalyst being stable to oxygen.

2. A method for producing vinyl-aromatic hydrocarbons, comprising dehydrogenating alkyl-aromatic hydrocarbons in the presence of the catalyst of claim 1.

3. A method for producing a catalyst for dehydrogenation of alkyl-aromatic hydrocarbons, which comprises reducing a potassium component-containing iron oxide composition with hydrogen at a temperature falling between 350 and 600° C., followed by oxidizing it with a vapor that contains oxygen molecules at a temperature falling between 250 and 500° C.

4. The method for producing a catalyst for dehydrogenation of alkyl-aromatic hydrocarbons as claimed in claim 3, wherein the oxygen molecules-containing vapor is air.

5. A method for producing vinyl-aromatic hydrocarbons, comprising dehydrogenating alkyl-aromatic hydrocarbons in the presence of the catalyst prepared by the method of claim 4.

6. A method for producing vinyl-aromatic hydrocarbons, comprising dehydrogenating alkyl-aromatic hydrocarbons in the presence of the catalyst prepared by the method of claim 3.

* * * * *